United States Patent [19]

Sarantakis

[11] 4,148,786
[45] Apr. 10, 1979

[54] ANALGESIC POLYPEPTIDE

[75] Inventor: Dimitrois Sarantakis, West Chester, Pa.

[73] Assignee: American Home Products Corporation, New York, N.Y.

[21] Appl. No.: 918,753

[22] Filed: Jun. 26, 1978

[51] Int. Cl.² ............... C07C 103/52; A61K 37/00
[52] U.S. Cl. .............................. 260/112.5 R; 424/177
[58] Field of Search .................. 260/112.5 R; 424/177

[56] References Cited
U.S. PATENT DOCUMENTS
4,028,319  6/1977  Jones, Jr. et al. ............. 260/112.5 R Primary Examiner—Delbert R. Phillips
Attorney, Agent, or Firm—Richard K. Jackson

[57] ABSTRACT

The polypeptides of the formula:

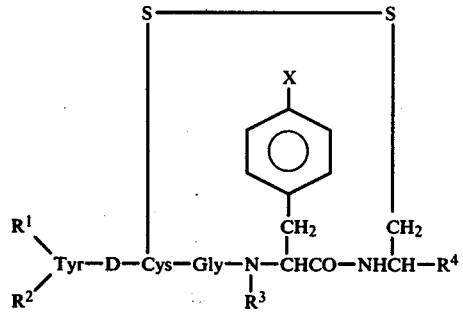

in which
 R$^1$ is hydrogen, lower alkyl, allyl, 2-isopentenyl, 3-isopentenyl, cyclopropylmethyl, cyclobutylmethyl, phenethyl or arginyl;
 R$^2$ is hydrogen or lower alkyl;
 R$^3$ is hydrogen or lower alkyl;
 R$^4$ is hydrogen, hydroxymethyl, carbo(lower)alkoxy, carbamyl or carboxy; and
 X is hydrogen, chloro, fluoro, bromo or iodo, the linear precursors thereof or a pharmaceutically acceptable salt thereof,
exert an analgesic effect in warm-blooded animals when peripherally administered.

9 Claims, No Drawings

ANALGESIC POLYPEPTIDE

BACKGROUND OF THE INVENTION

Enkephalin, a natural opiate receptor agonist in the brain, has been identified [see Hughes et al., Nature, 256, 557(1975)] as a mixture of two pentapeptides: H-Tyr-Gly-Gly-Phe-Met-OH (methionine-enkephalin) and H-Tyr-Gly-Gly-Phe-Leu-OH (leucine-enkephalin). Both peptides mimic the ability of morphine to block electrically evoked contractions of mouse vas deferens and guinea pig ileum, and both inhibit the sterospecific receptor binding of the opiate antagonist 3H-naloxone in brain homogenates.

It has been proposed that enkephalin receptors may be sites at which morphine-like drugs exert their analgesic activities, and that enekphalin may be the modulator or transmitter in brain systems for pain suppression or analgesia. It has been reported that methionine-enkephalin and leucine-enkephalin, when administered by injection in the brain ventricle in rats, induce a profound analgesia that is fully reversible by naloxone. [See Beluzzi et al., Nature, 260, 625(1976)]. The enkephalins are inactive when administered peripherally, however, and it is believed that the enkephalins are rapidly destroyed by blood enzymes and/or are poorly transported across the blood-brain barrier.

The amino acid sequence of methionine-enkephalin is identical to that of the N-terminal portion of the C-fragment ($\beta$-endorphin or $\beta$-LPH[61-91]) of the peptide $\beta$-lipotropin, which is found in large concentrations in the pituitary and in much lower concentrations in the brain. Other naturally-occurring fragments of $\beta$-lipotropin are known, for example: $\beta$-endorphin ($\beta$-LPH[61-76]) and $\gamma$-endorphin ($\beta$-LPH[61-77]). Both $\beta$-lipotropin and the endorphins show morphine-like properties in various test systems, and it has been suggested that methionine-enkephalin is a breakdown product of the large opiate-like peptides. Enkephalin, its relationship to $\beta$-lipotropin and the endorphins, and the pharmacological properties thereof, are reviewed in an article by Iversen et al., Nature, 262, 738(1976). Recent developments are also described in detail in the "Proceedings of the International Narcotics Research Club Meeting, Abderdeen, U.K., July 19–22, 1976," published in *OPIATES AND ENDOGENOUS OPIOID PEPTIDES*, North Holland Publishing Company, Amsterdam, 1976.

Various structural modifications of methionine-enkephalin and leucine-enkephalin are described in the literature. For example, H-Tyr-D-Ala-Gly-Phe-Met-NH$_2$ has been reported by Pert et al., Nature, 262, 738(1976) to produce long lasting analgesic after central administration. Bajusz et al., Acta. Biochem. Biophys. Acta. Sci. Hung., 11, 305(1976) report peripheral (i.v.) analgesic activity in rats for H-Tyr-D-Met-Gly-Phe-Pro-NH$_2$. Fredrickson, Life Sciences, 21, 23(1977) reported H-Tyr-D-Ala-Gly-Phe-D-Met-NH$_2$ produced analgesic activity in rats when centrally administered. The pentapeptide, H-Tyr-D-Ala-Gly-Phe-D-Leu-OH was shown by Baxter et al., Proc. of the B.P.S. page 456 (1977) to exhibit antinociceptive and behavioral effects in both rats and mice after central administration and by Wei et al., Life Sciences, 21, 321(1977) to exhibit peripheral analgesic activity.

DESCRIPTION OF THE INVENTION

In accoreance with this invention, there is provided a group of analgesic polypeptides of the formula:

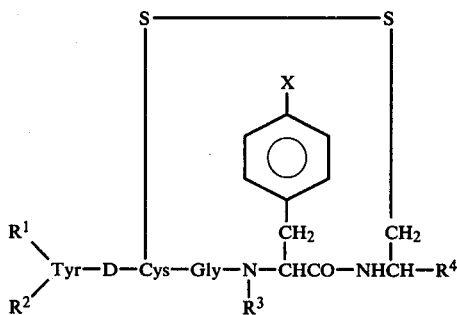

in which
- $R^1$ is hydrogen, lower alkyl, allyl, 2-isopentenyl, 3-isopentenyl, cyclopropylmethyl, cyclobutylmethyl, phenethyl or arginyl;
- $R^2$ is hydrogen or lower alkyl;
- $R^3$ is hydrogen or lower alkyl;
- $R^4$ is hydrogen, hydroxymethyl, carbo(lower)alkoxy, carbamyl or carboxy; and
- X is hydrogen, chloro, fluoro, bromo or iodo, the linear precursors thereof or a pharmaceutically acceptable salt thereof, exert an analgesic effect in warm-blooded animals when peripherally administered.

In the preceding definition of the compounds of this application, by the expression "lower alkyl" representing $R^1$, $R^2$ and $R^3$ as well as the lower alkyl ester function of $R^4$, applicant intends to embrace such groups as methyl, ethyl, propyl, butyl, pentyl and hexyl, with the understanding that an alkyl substituent of $\alpha$-amino nitrogen is preferably methyl while the ester $R^4$ may contain either a linear or branched chain alkyl group of from one to six carbon atoms.

The linear precursors of the compounds depicted above, which may be in the form of pharmaceutically acceptable salts, are the non-byclic, dimercapto polypeptides.

All chiral amino acid residues depiected in the preceding structural formula and elsewhere throughout the disclosure and the appended claims are in the natural or L-configuration except the C-terminal amino acid moiety which may be of either the D- or L-configuration and the indicated D-Cys in 2-position.

The pharmaceutically acceptable salts of the polypeptides of this invention are acid addition salts of the free base in which the acid may be either organic or inorganic, as for example, hydrochloric, phosphoric, maleic, acetic, citric, succinic, malic, and similar acids. Likewise, salts of the free peptidic acid are embraced by the expression "pharmaceutically acceptable salts", and include the sodium, potassium, ammonium, and lower alkylamine salts. The salts are prepared and isolated by conventional methods.

The analgesic polypeptides of this invention are prepared by typical solid phase procedures employing either a benzhydrylamine polystyrene based resin for the production of the C-terminal amides, which is the preferred group representing $R^4$, or a chloromethylated or hydroxy methylated divinyl benzene crosslinked polystyrene resin for production of the C-terminal carboxylic acid or esters. The polypeptide is removed from the resin support with HF and purified by gel filtration. The C-terminal methylol group is produced by standard techniques.

Those compounds devoid of C-terminal functionality ($R^4$=H) are produced either by conventional solution techniques or by preforming the appropriate polypeptide by the solid phase method followed by reaction with β-mercapto ethylamine.

The N-substituted tyrosine and phenylalanine derivatives employed in 1- and 4-positions of the polypeptide are prepared as reactants by reaction of methylchloride, allylchloride, cyclopropylmethyl chloride, etc. with a Boc protected ester of the appropriate amino acid in the presence of silver oxide. The product is then saponified and hydrolyzed to obtain the desired reactant.

The following examples illustrate the preparation of the polypeptides of the invention.

EXAMPLE 1 tert-Butyloxycarbonyl-O-2,6-dichlorobenzyl-L-tyrosyl-S-p-methoxybenzyl-D-cysteinyl-glycyl-L-phenylalanyl-S-p-methoxybenzyl-D-cysteinyl-benzhydrylamine polystyrene Eight grams of benzhydrylamine polystyrene resin (Peninsula Laboratories) with a substituting capacity of 0.4 mmoles/gram which had been neutralized with 12 percent triethylamine in DMF was treated in a solid phase reactor with Boc-D-Cys(SMBzl)-OH and 1M DIC in DMF to obtain the Boc-D-Cys(SMBzl)-substituted resin. The resin was then washed in the reaction in accordance with steps 11 and 12 of the following schedule A. The ninhydrin test was negative. Boc-Phe-OH, Boc-Gly-OH, Boc-D-Cys(SMBzl)-OH and Boc-Tyr(Cl$_2$Bzl)-OH were then incorporated individually into the peptido resin in accordance with the procedure set forth in schedule A to obtain the title compound.

Schedule A

1. Wash with $CH_2Cl_2 \times 3$.
2. Treat with TFA-$CH_2Cl_2$-EDT (1:1:5%, v/v) for 5 min.
3. Treat as in 2 for 25 min.
4. Wash with $CH_2Cl_2 \times 3$.
5. Wash with DMF.
6. Treat with 12% TEA in DMF twice for 3 min.
7. Wash with DMF.
8. Wash with $CH_2Cl_2 \times 3$.
9. Treat with 4 equivalents of the corresponding amino acid derivative in $CH_2Cl_2$-DMF and stir for 5 min.
10. Add in two portions 5 equivalents of DIC dissolved in $CH_2Cl_2$ and over a period of 30 min. Reaction time 6 hours.
11. Wash with DMF $\times$ 3.
12. Wash with $CH_2Cl_2 \times 3$.
13. Test ninhydrin reaction according to Kaiser et al., *Annal. Biochem.* 34, 595(1970). In case of incomplete reaction repeat lines 9 to 13 as above.

EXAMPLE 2

L-Tyrosyl-D-cysteinyl-glycyl-L-phenylalanyl-D-cysteinyl amide cyclic (2-5) disulfide The peptidoresin of the previous example was mixed with anisole (20 ml.) and treated with liquid anhydrous HF in the absence of air for 45 minutes at 20° C. The excess HF was evaporated in vacuo as fast as possible and the residue was taken in 20% aqueous acetic acid and filtered. The filtrate was poured into 6 liters of degassed water, the pH was adjusted to 7 with dilute $NH_4OH$, and the mixture was stirred overnight in the open air. The pH was adjusted to 5 with glacial acetic acid and the peptidic material was absorbed onto Amberlite CG-50 (H$^+$ form). The peptidic material was eluted with a mixture of Water-acetic acid-pyridine 66:4:30, v/v and the fractions containing the peptide were pooled and lyophilized to yield crude material. This crude material was chromatographed through a column of Sephadex G-10 (2.7 $\times$ 70 cm.) and eluted with 15% aqueous acetic acid. The material which emerged in fractions (5.5 ml. each) 50–73 was pooled and lyophilized to yield 591 mg. of slightly impure product. This product was chromatographed through a column of Sephadex LH 20 (1.9 $\times$ 90 cm.) equilibrated with 85% ethanol and eluted with the same solvent. The material which emerged in fractions 57–60 was lyophilized to yield 198 mg. of the title compound.

TLC, silica gel precoated plates, Brinkmann, Rf (BWA, 4:1:1, v/v) 0.55, Rf (B-EA-W-A, 1:1:1:1, v/v) 0.65, Rf (tAmOH-W-P, 7:6:7, v/v) 0.50.

Amino acid analysis: Gly (1) 1, Tyr (1) 1, Phe (1) 0.96, $NH_3$ (1) 1.14, Cys, N.D.

EXAMPLE 3

L-Tyrosyl-D-Cysteinyl-glycyl-L-phenylalanyl-L-cysteinyl amide cyclic (2-5) disulfide The compound was prepared in the manner set forth in Examples 1 and 2.

TLC, silica gel precoated glass plates (Analtech) Rf(BWA, 4:1:1, v/v) 0.50, Rf (BWA, 4:5:1, v/v) 0.59.

Amino acid analysis: Gly (1) 1, Cys (2) 1.63, Try (1) 0.84, Phe (1) 0.99, $NH_3$ (1) 1.38.

EXAMPLE 4

L-Tyrosyl-D-cysteinyl-glycyl-N-methyl-L-phenylalanyl-D-cysteinylamide cyclic (2-5) disulfide The compound was prepared in the manner set forth in Examples 1 and 2.

TLC, silica gel G precoated glass plates, (Analtech) Rf(BWA, 4:1:1, v/v) 0.60, Rf(t-AmOH-W-P, 7:6:7, v/v) 0.82

Amino acid analysis: Gly (1) 1, Cys (2) 1.72, Tyr (1) 1.04, $NH_3$ (1) 1.21, N(Me)Phe, N.D.

EXAMPLE 5

L-Arginyl-L-tyrosyl-D-cysteinyl-glycyl-L-phenylalanyl-D-cysteinylamide cyclic (3-6) disulfide The compound was prepared in the manner set forth in Examples 1 and 2.

TLC, silica gel precoated glass plates, (Analtech) Rf (BWA, 4:1:1, v/v) 0.30, Rf (BWA, 4:5:1, v/v) 0.37.

Amino acid analysis: Gly (1) 1.02, Cys (2) 1.72, Tyr (1) 0.97, Phe (1) 4.00, $NH_3$ (1) 1.16, Arg (1) 0.97.

EXAMPLE 6

N-Methyl-L-tyrosyl-D-cysteinyl-glycyl-L-phenylalanyl-D-cysteinylamide cyclic (2-5) disulfide The compound was prepared following the procedure set forth in Examples 1 and 2.

TLC, silica gel precoated glass plates, (Analtech) Rf (BWA, 4:1:1, v/v) 0.58, Rf (t-AmOH-W-P, 7:6:7, v/v) 0.98.

Amino acid analysis: Gly (1) 1, Cys N.D., Phe (1) 0.99, N(Me)Tyr N.D., $NH_3$(1) 1.05.

The analgesic activity of the polypeptides of this invention was demonstrated by the standard rat-tail flick test of D'Amour and Smith, J. Pharmacol. Exp. Ther., 72, 74(1941), whereby groups of six male rats (150–200 gms.) were placed in individual holders. The holders were situated so that a high intensity light beam would shine on the tip of the rats tail. The light beam intensity was adjusted so that normal rats respond by removing their tails from the light stimulus within from 3 to 8 seconds. The average of three time readings for removal of a rats tail from the light beam, taken 20 minutes apart serves as a pre-drug control. The rats were selected for use based upon control readings that agreed within one second. The compounds of this invention were then administered intravenously and the test performed at 15, 30 and 60 minutes to determine the animals reaction time which was compared with the control average and tested for significance. The number of rats showing analgesia at each time period out of the total group for each dose administered is noted as a ratio and the number of positive responses observed is relative to the total number of challenges for each group of rats. The following Table summarizes the data obtained:

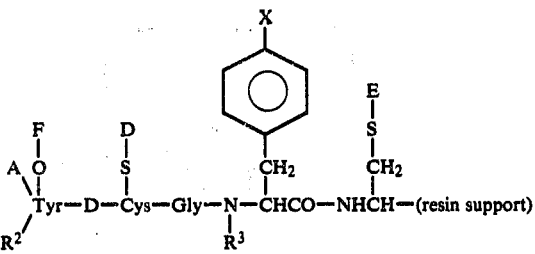

in which

R$^2$, R$^3$ and X are defined supra,

A is hydrogen or an α-amino protecting group or alpha amino protected N-guanyl protected arginyl;

F is a protecting group for the phenolic hydroxy group of tyrosyl;

D is a protecting group for the mercapto group of D-cysteinyl, and

E is a protecting group for the mercapto group of the

| Compound | Dose (mg/kg) | TIME (minutes) No. Analgesic Total No. Tested | | | Positive Responses Total Possible Responses | Comments |
|---|---|---|---|---|---|---|
| | | 15 | 30 | 60 | | |
| Example 2 | 5.0 iv | 5/5 | 5/5 | 4/4 | 14/14 | 4/4 Respiration very depressed 2/6 dead |
| | 1.0 iv | 4/5 | 4/4 | 2/3 | 10/12 | 2/3 severe respiratory depression 3/6 dead |
| | 1 iv | 4/6 | 5/6 | 3/6 | 12/18 | Slight depression |
| | 0.5 iv | 3/6 | 2/6 | 1/6 | 6/10 | |
| | 0.5 iv | 4/6 | 3/6 | 2/6 | 9/18 | 1/6 slight respiratory depression |
| | 0.1 iv | 2/6 | 0/6 | 0/6 | 2/18 | |
| | 5 s.c. | 4/6 | | | 7/24 | |
| Example 3 | 5 iv | 6/6 | 5/6 | 4/6 | 15/18 | 3/6 moderate to severe respiratory depression |
| | 1 iv | 4/6 | 2/6 | 1/6 | 7/18 | |
| Example 4 | 5 iv | 5/6 | 4/6 | 3/6 | 12/18 | 3/6 respiratory depression |
| Example 5 | 5 iv | 6/6 | 5/5 | 5/5 | 16/16 | 3/5 respiratory depression 1 dead |
| | 1 iv | 4/6 | 3/6 | 2/6 | 9/18 | |
| | 0.5 iv | 2/6 | 2/6 | 0/6 | 4/18 | |
| Example 6 | 5 iv | 6/6 | 4/4 | 3/3 | 13/13 | 3/3 respiratory depression 3 dead |
| | 1 iv | 6/6 | 5/6 | 3/6 | 14/18 | |

The opiate receptor binding affinity of the compound of Example 2 was determined following the method of Chang et al., Life Sciences, 18, 1473–82(1976). The product of Example 2 demonstrated in two assays, a displacement potency 100 and 109 times that of morphine.

The test results demonstrate that the compounds of this invention induce analgesia upon administration of a single intravenous injection at a dose as low as 0.1 milligrams per kilogram. For practical purposes, it is contemplated, based upon the proceding test results, that a dose of from about 0.1 to about 5 milligrams per kilogram in single or plural doses is the appropriate dosage to achieve that degree of analgesia desired for various applications. The exact dose to be employed will, of course, vary with the specific compound employed, the patient and the degree of analgesia desired. The determination of a precise dose for production of a desired effect is readily determined empirically by the physician.

The protected intermediates for the linear and cyclic polypeptides disclosed herein form an additional aspect of the invention. The intermediates are of the formula:

C-terminal moiety.

Of the many protecting groups known to the art for use in conjunction with each of the functional groups found in the depicted polypeptide intermediate, the most preferred are tert-butyloxycarbonyl (Boc) for the α-amino group of the arginyl or tyrosyl moiety, nitro (NO$_2$) for the guanyl group of the arginyl moiety, 2,6-dichlorobenzyl (Cl$_2$Bzl) for the phenolic hydroxyl group of the tyrosyl moiety, p-methoxybenzyl (MBzl) for the mercapto group of the D-cysteinyl moiety and the C-terminal moiety. Because the C-terminal amides are the preferred final products, the resin support in the intermediates is preferably a benzhydrylamine polystyrene resin.

What is claimed is:

1. A polypeptide of the formula:

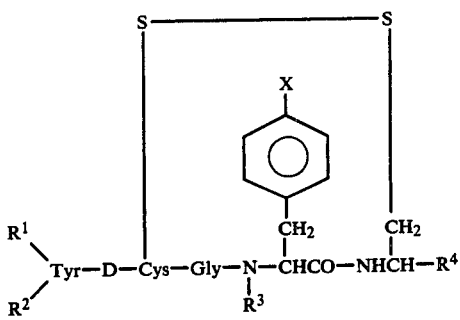

in which
- R¹ is hydrogen, lower alkyl, allyl, 2-isopentenyl, 3-isopentenyl, cyclopropylmethyl, cyclobutylmethyl, phenethyl or arginyl;
- R² is hydrogen or lower alkyl;
- R³ is hydrogen or lower alkyl;
- R⁴ is hydrogen, hydroxymethyl, carbo(lower)alkoxy, carbamyl or carboxy; and
- X is hydrogen, chloro, fluoro, bromo or iodo;

the linear precursors thereof or a pharmaceutically acceptable salt thereof.

2. A compound of claim 1 which is Tyr-D-Cys-Gly-Phe-D-Cys-NH₂ cyclic (2-5) disulfide, its linear precursor or a pharmaceuticaly acceptable salt thereof.

3. A compound of claim 1 which is Tyr-D-Cys-Gly-Phe-Cys-NH₂ cyclic (2-5) disulfide, its linear precursor or a pharmaceutically acceptable salt thereof.

4. A compound of claim 1 which is Tyr-D-Cys-Gly-N-methyl-Phe-D-Cys-NH₂ cyclic (2-5) disulfide, its linear precursor or a pharmaceutically acceptable salt thereof.

5. A compound of claim 1 which is Arg-Tyr-D-Cys-Gly-Phe-D-Cys-NH₂ cyclic (3-6) disulfide, its linear precursor or a pharmaceutically acceptable salt thereof.

6. A compound of claim 1 which is N-methyl-Tyr-D-Cys-Gly-Phe-D-Cys-NH₂ cyclic (2-5) disulfide, its linear precursor or a pharmaceutically acceptable salt thereof.

7. A compound of the formula:

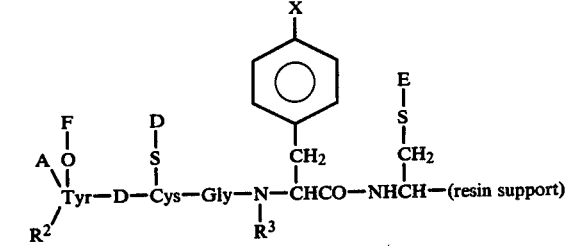

in which
- R² is hydrogen or lower alkyl;
- R³ is hydrogen or lower alkyl;
- X is hydrogen, chloro, bromo, fluoro or iodo;
- A is hydrogen, an α-amino protecting group or α-amino protected, N-guanyl protected arginyl;
- F is a phenolic hydroxy protecting group;
- D is a mercapto protecting group; and
- E is a mercapto protecting group.

8. A compound of claim 7 in which A is tert-butyloxycarbonyl-(Nᵍ-NO₂)Arg, F is 2,6-dichlorobenzyl, D is p-methoxybenzyl and E is p-methoxybenzyl.

9. A compound of claim 7 in which A is tert-butyloxycarbonyl, F is 2,6-dichlorobenzyl, D is p-methoxybenzyl and E is p-methoxybenzyl.

* * * * *